US007449295B2

(12) United States Patent
Hashmi et al.

(10) Patent No.: US 7,449,295 B2
(45) Date of Patent: Nov. 11, 2008

(54) METHOD OF NUCLEIC ACID TYPING FOR SELECTING REGISTERED DONORS FOR CROSS-MATCHING TO TRANSFUSION RECIPIENTS

(75) Inventors: Ghazala Hashmi, Holmdel, NJ (US); Michael Seul, Fanwood, NJ (US); Marion E. Reid, Jamaica Estates, NY (US); Michael Pierce, Flemington, NJ (US)

(73) Assignees: Bio Array Solutions, Warren, NJ (US); New York Blood Center, New York, NY (US)

( * ) Notice: Subject to any disclaimer, the term of this patent is extended or adjusted under 35 U.S.C. 154(b) by 321 days.

(21) Appl. No.: 11/257,285

(22) Filed: Oct. 24, 2005

(65) Prior Publication Data

US 2006/0105370 A1      May 18, 2006

Related U.S. Application Data

(60) Provisional application No. 60/621,196, filed on Oct. 22, 2004.

(51) Int. Cl.
*C12Q 1/68* (2006.01)
(52) U.S. Cl. .......................................................... 435/6
(58) Field of Classification Search ........................ None
See application file for complete search history.

(56) References Cited

FOREIGN PATENT DOCUMENTS

EP            1591534         11/2005
WO        WO 03034029         4/2003
WO     WO-2005095650 A1 *   10/2005

OTHER PUBLICATIONS

Beiboer, Sigrid H.W., et al., "Rapid Genotyping of Blood Group Antigens by Multiplex Polymerase Chain Reaction and DNA Microarray Hybridization," *Transfusion* 45: 667-679 (May 2005).
PCT Search Report PCT/US05/38296 (2006).
S.W. Beiboer et al. "Rapid Genotyping of Blood Group Antigens by Multiplex Polymerase Chain Reaction and DNA Microarray Hybridization" 45 Transfusion 667-679 (2005).
M.E. Reid et al. "Novel Dombrock Blood Group Genetic Variants . . . " Blood (ASH Annual Meeting Abstracts) 2004, 104:Abstract 383.
M. St-Loius et al. "Extended Blood Grouping of Blood Donors . . . " Transfusion 43: 1126-1132 (2003).
M.E. Reid "The Dombrock Blood Group System: a Review" Transfusion 43: 107-114 (2003).
Y.X. Chen et al. "Deletion of Arginine Codon 229 . . . " Transfusion 44: 391-398 (2004).
E. Strobel et al. "The molecular basis of Rhesus antigen E" Transfusion 44: 407-09 (2004).

* cited by examiner

*Primary Examiner*—James Martinell
(74) *Attorney, Agent, or Firm*—Eric P. Mirabel (57) ABSTRACT

Disclosed are a method and an algorithm for genetic cross-matching based on the comparison of recipient and donor genotypes—and the underlying combinations of alleles and haplotypes. The method of the invention, rather than focusing on phenotype prediction, instead relies on a comparison of genetic variants identified in the recipient and available donors, whose information preferably will be compiled in a widely available donor registry, to maximize molecular compatibility. The genotypes can be matched based on the weighted clinical significance of a genotypic difference between donor and recipient, such that certain mismatches are more acceptable than others.

25 Claims, 2 Drawing Sheets

Fig. 1A: DoA

Fig. 1B: HY

SEQUENCE LISTING

<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: Artificial Primer

<400> SEQUENCE: 1
gctatttgct cctttgacca c    21

```
<210> SEQ ID NO 2
<211> LENGTH: 18
<212> TYPE: DNA
<213> ORGANISM: Artificial Sequence
<220> FEATURE:
<223> OTHER INFORMATION: Artificial Primer

<400> SEQUENCE: 2
tctccccaca gagcagtt                                                 18

<210> SEQ ID NO 3
<211> LENGTH: 24
<212> TYPE: DNA
<213> ORGANISM: Artificial Sequence
<220> FEATURE:
<223> OTHER INFORMATION: Artificial Primer

<400> SEQUENCE: 3
cctcaagtga tctgccttcc tcag                                          24

<210> SEQ ID NO 4
<211> LENGTH: 22
<212> TYPE: DNA
<213> ORGANISM: Artificial Sequence
<220> FEATURE:
<223> OTHER INFORMATION: Artificial Primer

<400> SEQUENCE: 4
tgctcaccat tctgatcttc ct                                            22

<210> SEQ ID NO 5
<211> LENGTH: 21
<212> TYPE: DNA
<213> ORGANISM: Artificial Sequence
<220> FEATURE:
<223> OTHER INFORMATION: Artificial Primer

<400> SEQUENCE: 5
catctccgtc aggcactcca t                                             21
```

METHOD OF NUCLEIC ACID TYPING FOR SELECTING REGISTERED DONORS FOR CROSS-MATCHING TO TRANSFUSION RECIPIENTS

RELATED APPLICATIONS

This Application claims priority to U.S. Provisional Application No. 60/621,196, filed Oct. 22, 2004.

BACKGROUND

The identification of antibodies and the provision of antigen-negative blood forms the basis for safe blood transfusion by minimizing the risk of adverse transfusion reactions, triggered when antibodies circulating in the patient's blood stream encounter antigens displayed on a donor's erythrocytes. Current practice in transfusion medicine provides for the serological typing and labeling of all donor blood for ABO and RHD antigens to facilitate the matching of red blood cell components to the recipient's blood type. The further reduction of allo-immunization remains an important clinical concern, and therefore it would be highly desirable to match additional blood group antigens. However, this practice is precluded by the lack of appropriate antisera, and the complexity of labor-intensive serological typing protocols, particularly when encountering multiple allo-antibodies. As a result, most donor centers screen only a selected cohort of donors and maintain limited inventory of antigen-negative units. This practice can introduce delays in treatment and thus create significant additional expense in patient care, and also can exacerbate emergency situations.

Comprehensive donor DNA typing of donors, as recently described (see Reid et al., Transfusion May 2005) will enable donor centers to maintain a registry of prospective donors, and large and diverse inventories of fully characterized blood products available for instant shipping. In addition, the analysis of blood group genes at the DNA level provides a detailed picture of the allelic diversity that underlies phenotypic variability, an approach which helps in addressing clinical problems that cannot be addressed by serological techniques, such as determination of antigen types for which the available antibodies are weakly reactive, the analysis of recently transfused patients, or the identification of fetuses at risk for hemolytic disease of the newborn. Although the genotype may not reflect the phenotype, DNA analysis will identify the potential antigen-negative which, if desirable, can be confirmed by classical hemagglutination. Comprehensive DNA typing also can be extended to recipients and indeed can be applied population-wide by invoking practical methodologies, preferably eMAP™, performed on a BeadChip™ platform (See U.S. application Ser. No. 10/271,602, incorporated herein by reference).

Genetic Cross-Matching

A match, or near-match, between selected marker identified in a recipient, and in candidate donors of transfused blood—the markers corresponding to polymorphic sites located in genes encoding blood group antigens and specifically including minor blood group antigen—generally will minimize the risk of recipient immunization and, in immunized recipients, the risk of alloantibody-mediated adverse immune reactions following transfusion. That is, if the set of markers is selected to probe the relevant alleles associated with clinically significant hemolytic transfusion reactions ("allo-reactions"), then a comparison of markers of recipient and donor will permit the selection of donors that are genetically compatible with a given recipient. For example, each of a set of monozygotic twins, genetically identical, would be the ideal donor for the other. In the case of transfusion, the requirement of genetic identity—or near-identity—of recipient and candidate donor is limited to a set of relevant genes which—when expressed—encode certain human erythrocyte antigens (HEA) displayed on blood-borne cells against which the recipient either already has made (on the basis of earlier exposure) antibodies ("allo-antibodies") or can make antibodies. Thus, markers correlating with human erythrocyte antigens (HEA) including the "major" antigens (A, B and Rh) as well as a number of clinically relevant "minor" antigens (e.g., Duffy, Kell, Kidd, MNS, Dombrock and others), as discussed in U.S. application Ser. No. 11/168,224, are of interest.

The benefit of such a genetic cross-matching procedure will be to minimize or reduce not only the risk of adverse immune reactions, but also the risk of immunizing recipients in the first place, to eliminate the need for and to enable the rapid selection of blood products for transfusion from a group of registered and fully characterized donors, also referred to herein as a donor registry. Once fully implemented, genetic implemented, genetic cross-matching will eliminate the narrowing bottleneck created by the increasing cost of serological reagents and complex and labor-intensive protocols as well as the need for repeat testing.

SUMMARY

Disclosed are a method and an algorithm for genetic cross-matching based on the comparison of recipient and donor genotypes—and the underlying combinations of alleles and haplotypes. Preferably, as described, in a co-pending application, entitled "Multiplexed Analysis of Polymorphic Loci by Concurrent Interrogation and Enzyme-Mediated Detection," filed Oct. 15, 2002, Ser. No. 10/271,602 (incorporated by reference), genotypes are determined in a single ("multiplexed") test to permit rapid, large-scale typing. The method of the invention, rather than focusing on phenotype prediction as advocated in conventional procedures, instead relies on a comparison of genetic variants identified in the recipient and available donors, whose information preferably will be compiled in a widely available donor registry, to maximize molecular compatibility. Using, for example, a BeadChip™ format such as disclosed herein, to enable, at reasonable cost, large-scale comprehensive genotyping of clinically relevant transfusion antigens, preferably performed in a neonatal screening context, would permit the transfusion antigen genotype ("TAG")—and related genetic information—to become part of individual medical records which could be stored in a readily accessible format such as implantable chips, or other electronic tags carried, for example, in bracelets.

DETAILED DESCRIPTION

For present purposes, we define a genotype as a string of markers at selected polymorphic sites (also referred to herein as alleles); that is, values giving the configuration of target nucleic acid markers located within one or more genes of interest. Preferably, each designated site is interrogated with a pair of elongation probes of which one is designed to detect the normal (N) allele, the other to detect a specific variant (V) allele, under conditions ensuring that polymerase-catalyzed probe elongation occurs for matched probes, that is those matched to the allele at the 3'-terminus, but not for mismatched probes. The pattern of assay signal intensities representing the yield of individual probe elongation reactions in accordance with this eMAP™ format (see Ser. No. 10/271,602, supra), is converted to a discrete reaction pattern—by application of preset thresholds—to ratios (or other combinations) of assay signal intensities associated with probes within a pair of probes directed against each marker.

A genotype then is represented by a string, $G=\{(NV)_{ik}\}$ where i enumerates the genes in the set of selected genes of interest, and k enumerates designated polymorphic sites within the i-th gene, and where the pair (NV) can assume values of AA, AB (or BA) and BB. In a preferred embodiment, the signal intensities associated with a pair of probes directed to the same marker, preferably corrected by removing non-specific ("background") contributions, and one such intensity, $i_N$, representing the amount of normal allele, and the other such intensity, $i_V$, representing the amount of variant allele in the sample, are combined to form the discrimination parameter $\Delta=(i_N-i_V)/(i_N+i_V)$, a quantity which varies between −1 and 1. For a given sample, a value of $\Delta$ below a preset lower threshold indicates a call of homozygous normal, a value of $\Delta$ above a preset upper threshold indicates a call of homozygous variant, and a value of $\Delta$ above the lower and below the upper threshold indicates a call of heterozygous. A transfusion antigen genotype is represented by a string, $G=\{\Delta_{ik}\}$, where, as before, i enumerates the genes in the set of selected genes of interest, and k enumerates designated polymorphic markers within the i-th gene. Accordingly, a transfusion antigen genotype is designated herein either in the representation AA, AB (or BA) and BB or, equivalently, in the representation 1, 0, −1.

Assigning Alleles: Decomposition of Genotypes into Haplotypes—Expressed antigenic determinants reflect the specific allelic combinations of the encoding genes. A genotype generally represents a combination of two constituent haplotype strings, here denoted H1 and H2, each in the form of a ternary string such that H1 OR H2 generates the genotype. All compatible 2-string combinations are determined in a process also referred to herein as allele assignment or automated allele analysis ("AAA"), preferably performed automatically, using a program such as the AAA program for Automated Allele Analysis, elaborated in co-pending application, entitled: "Automated Analysis of Multiplexed Probe Target Interaction Patterns: Pattern Matching and Allele Identification," filed Aug. 2, 2004, Ser. No. 10/909,638 (incorporated by reference).

This application also discloses a method of "error correction" wherein a reaction pattern (of probes-targets) generated from an assay is compared, digit by digit, to the possible reaction patterns, that is, strings representing 2-allele combinations of known alleles; a list of such reference strings is also referred to herein as a hit table. For digits which do not match, the error correction is by way of changing individual digits in the string as judged necessary in order to produce a match with a valid reference string (generated from known allele combinations).

Several allele or haplotype combinations generally may be compatible with a single genotype, as illustrated in an Example below, and this issue is addressed herein by an application of the "phasing" methodology previously disclosed in Ser. No. 10/271,602, supra.

Donor Registry—Assuming, without loss of generality, application of the preferred embodiment of multiplex genotype determination, genotypes of prospective donors are determined in accordance with the eMAP format. In a preferred embodiment, the genotype, and the set of constituent allele or haplotype combinations, are stored in form of a list of records, in an appropriate database format, such as MicroSoft Access or SQL, as follows:

$\{G=\{(N,V)_{ik}\}; \{\text{Haplotype Combinations}\}; 1\leq i\leq \Gamma; 1\leq k\leq M(i); p\}$, or $\{G=\{\Delta_{ik}\}; \{\text{Haplotype Combinations}\}; 1\leq i\leq \Gamma; 1\leq k\leq M(i); p\}$, where $\Gamma$ denotes the number of selected genes, such as those encoding blood group antigens, M(i) denotes the number of markers in the i-th gene and p denotes the address ("pointer") associated with a memory location, for example in a database such as an inventory, containing a list of donors of given genotype. Within the inventory, compatible donors may be sorted by additional criteria such as date of sample collection, completeness of characterization (e.g., knowledge of additional antigen types such as HLA or HPA), age, gender, etc.

Selection Designated Polymorphic Sites and Table of Associated Weights—A mismatch between patient and donor alleles or haplotypes can lead to immunization, or to adverse immune reactions of differing severity, mediated by antibodies circulating within the patient's serum recognizing expressed epitopes that are encoded by donor marker alleles (or antigenic determinants). To represent this degree of significance, the invention introduces a set of numerical weights, $w_{ik}$, associated with the k-th designated marker on the i-th gene of interest. The relative magnitude of these weights reflects the severity of known or anticipated transfusion reactions associated with a mismatch at the corresponding site, and the allo-reaction(s) associated with a mismatch of the corresponding phenotypes. As illustrated in Tables 1 and 2, weights may be chosen to reflect empirical measures of clinical significance such as NONE (0), MILD (1), MILD-TO-SEVERE (3), SEVERE (5). Silencing mutations producing a null phenotype in the donor generally will enhance compatibility given the absence of the corresponding antigen. If allo-antibodies have been identified, the corresponding cognate antigen and associated markers are given a high weight, reflecting the clinical significance of the antibody, as shown in Table 4.

Matching Alleles of Genotypically Identical Recipient and Donor: Dombrock

This example uses three markers in the Dombrock system, associated with $Do^a/Do^b$, namely: $M_1$ (378 C>T); $M_2$ (624 T>C); $M_3$ (793 A>G) to illustrate the matching of a genotypically identical recipient and prospective donor.

A reaction pattern representing the interaction of a set of probe pairs and target (where one probe in a pair can indicate the presence of a "normal" allele, and the other probe in the pair indicates the presence of a "variant" allele) can be generated using, e.g., the eMAP assay format with a set of probe pairs capable of annealing to Dombrock genes (or amplicons or targets derived from Dombrock genes by PCR amplification or otherwise). For the three selected markers, a possible reaction pattern is: AB AB AB, that is a reaction pattern: 0, 0, 0. In a diploid genome, a particular reaction pattern corresponds to a combination of at least two alleles. Thus, this reaction pattern is first decomposed into the patterns represented by combinations of alleles, in this case either of the following (see Table 4):

AB AB AB=AAA OR BBB; that is DoA or DoB alternatively:

AB BA AB=AB BA BA=ABB OR BAA; that is Hy or Jo where "A" designates a normal allele and "B" designates the variant. Next, a "mismatch matrix" is constructed which indicates by application of weights, the severity of adverse clinical outcomes resulting from a mismatch. In the present case:

|     | AAA | BBB       | BAA       | ABB       |
|-----|-----|-----------|-----------|-----------|
| AAA | 0   | $w_3$     | $w_2$     | $w_2 + w_3$ |
| BBB |     | 0         | $w_2 + w_3$ | $w_2$   |
| BAA |     |           | 0         | $w_3$     |
| ABB |     |           |           | 0         |

Where weighting is applied to a mismatch in the allele (of the gene of interest, here Dombrock). These weights, preferably in a separate look-up table, might be, w1=1, w2=5, w3=5 (or other preset values, that are informed by empirical knowledge relating to clinical significance).

Resolving Allelic Ambiguities by "Phasing"

Multiple biallelic combinations may be compatible with a specific genotype determined over a set of selected markers. Matching of a recipient with a known genotype, $G_R$, to a compatible donor of the same genotype requires matching of the actual underlying set of alleles (or haplotypes). These can be established by the following phasing strategy which establishes 2-point correlations (see also US Publication No. 20040002073A1, incorporated by reference). The strategy entails probing of bead-displayed elongation products using tagged hybridization probes, either one at a time (in multiple rounds of annealing and deannealing) or in a parallel process, preferably involving multiple colors of detection, where preferably in such a case, the elongation product itself is not labeled.

Figure 1A:
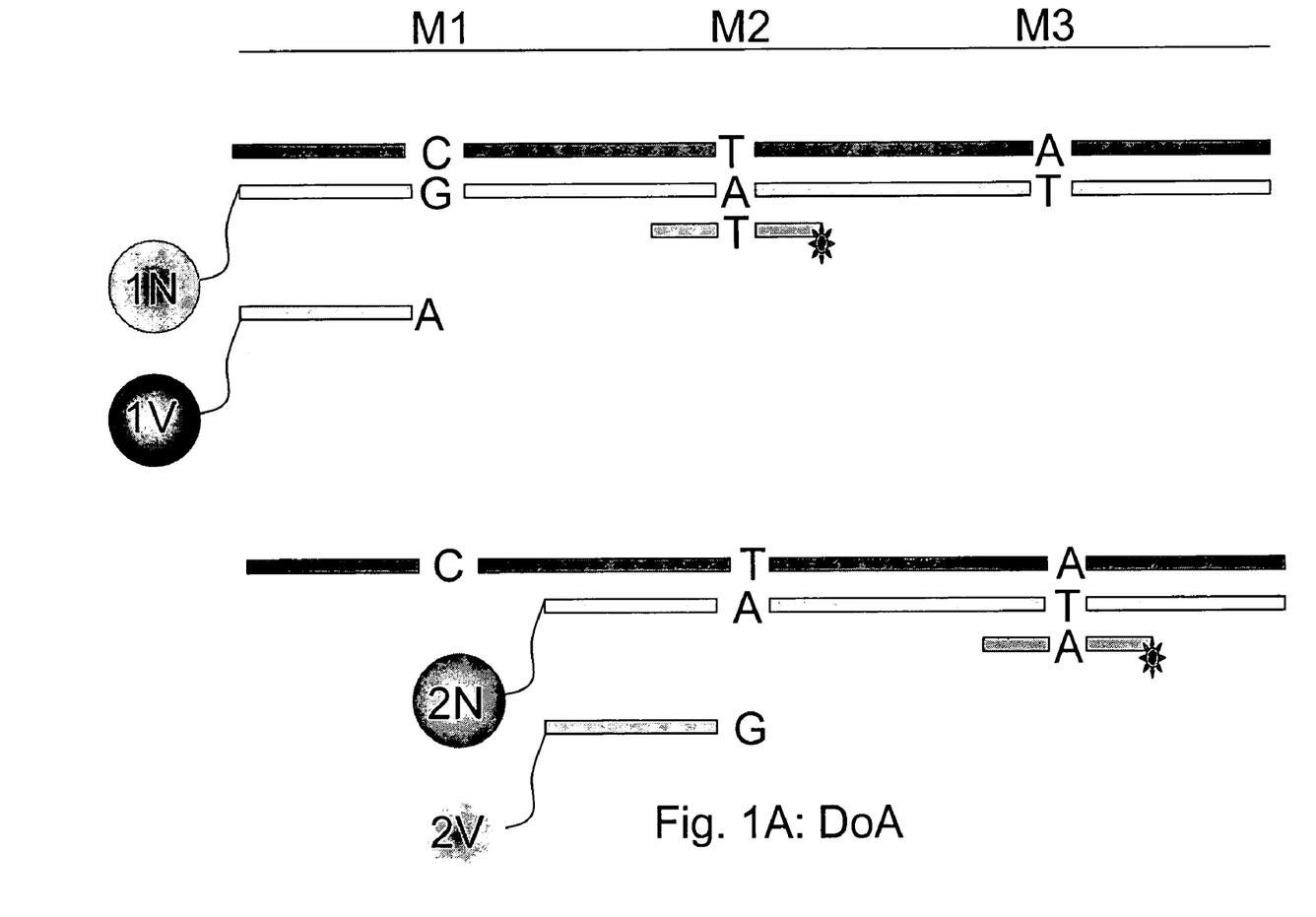
FIGS. 1A and 1B illustrates use of multiple encoded probes to resolve ambiguity through phasing.
Figure 1B:
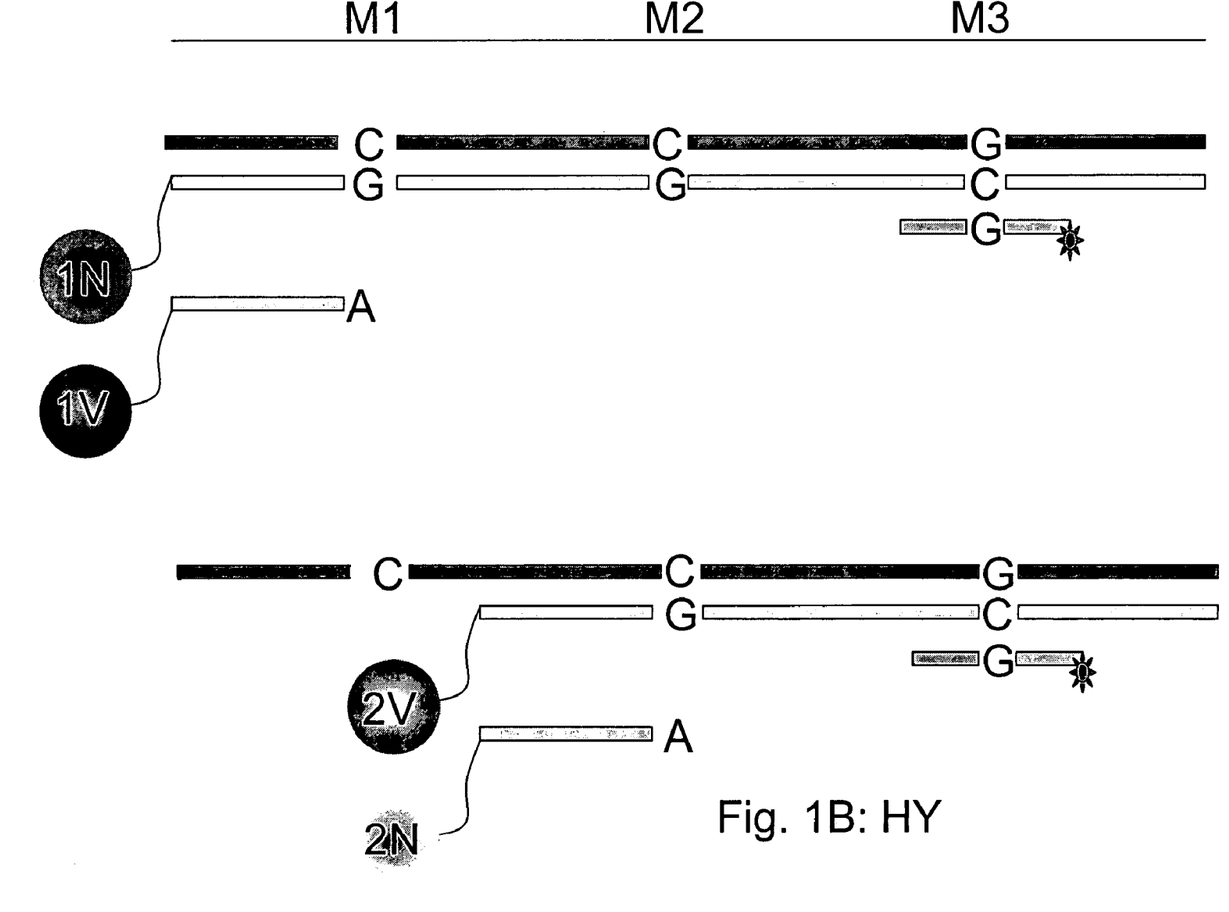

This is illustrated in FIGS. 1A and 1B, where markers M1, M2 and M3 (with polymorphic sites which can be C, T or A, respectively, as in the first allele (corresponding to DoA), or C, C, G, respectively, as in the second allele (corresponding to Hy), or other nucleotides) are interrogated using tagged probes. Differentially labeled extendable probes are used for detection of a first allele, where probe "1N" (directed to marker M1) has a "G" nucleotide at the 3' terminus, probe "1V" (also directed to marker M1) has an a "A" nucleotide at the 3' terminus, probe "2N" (directed to marker M2) has an "A" nucleotide at the 3' terminus, probe "2V" (also directed to marker M2) has a "G" nucleotide at the 3' terminus. Depending on the M1, M2 and M3 marker combinations, different combinations of the probes are elongated, generating different signal intensity patterns as interaction products interact with tagged probes, as shown in FIGS. 1A and 1B. Thus, if DoA is encountered (FIG. 1A), probe 1N is elongated, and decorated by a fluorescent probe annealing to the elongation product at the position of marker M2; conversely, if Hy is encountered (FIG. 1B), probe 2V is elongated, and decorated by a fluorescent probe annealing to the elongation product at the position of marker M3. The signal intensity pattern produced by addition of fluoresceinated probes (directed to markers M2 and/or M3, as shown) identifies either DoA and thus DoA OR DoB as the combination represented by the reaction pattern 0, 0, 0, or identifies Hy and thus Hy OR Jo as the combination represented by the reaction pattern 0, 0, 0. That is, phasing resolves the ambiguity.

Genetic Cross Matching: Distance between Haplotypes—Given a recipient genotype, preferably in the representation representing at least a substring of available donor genotypes (of one or more donors of identical genotype to the recipient), they are identified by haplotype (string) matching. Here, the recipient haplotype preferably comprises at least the set of marker alleles represented in the corresponding haplotype of available donors. In one embodiment, each of the strings, $H_2$, $H_R$ is compared to the set of strings, {H}, in a donor database, and matches are ranked in the order of an increasing weighted Hamming distance where the weights are preset so as to reflect clinical severity, as discussed in connection with the discussion of the mismatch matrix. For example, assuming there to be M mismatched alleles, a possible distance function is:

$$\Pi^2 = (1/M) \, 3_{mismatched\ alleles} \, w^2$$

Implementation—Preferably, a computer program implementing a string matching algorithm is used to perform the genetic cross matching automatically, to list available donor in the order of increasing $\Pi^2$ (or equivalent distance function) up to a maximal distance between patient and donor strings.

The pseudocode below summarizes the string matching algorithm (the terms "allele" and "haplotype" are used interchangeably). To optimize execution speed in handling the large data bases of interest, the implementation, such as that within wAAA™ (U.S. Ser. No. 10/909,638, supra), employs suitable data structures and invokes integer arithmetic.

```
SelectCompatibleDonors(DonorRegistry, RecipientHaplotypes);
{
    AssignAlleles(RecipientHaplotypes, DonorHaplotypes);
}
AssignAlleles(AlleleArray1, AlleleAray2, ReactionStr, hitTable);
{
    /*
    ** for each allele in hit table, determine mismatch with reaction pattern of
    ** interest, Allele0 is the first allele entry in hit table AlleleN is the last allele
    ** entry in hit table
    */
    minMismatch = 30;                      /* initiate to large number
                                             */
    FOR (A1=Allele0; A1≦AlleleN; A1++)
    {
        A1Hit = getHitStr(A1, hitTable);   /* retrieve from hit table
                                             string representing allele
                                             A1 */
        FOR(A2=A1; A2≦AlleleN; A2++)
        {
            A2Hit = getHitStr(A2, hitTable);
            combStr = OR(A1Hit, A2Hit);    /* construct allele
```

```
                    combination by applying
                    OR operation */
    /*
    ** evaluate degree of mismatch between hitStr and reactionStr;
    ** speed up: if mismatch exceeds minMismatch + 2, quit loop
    */
        nMismatch = Compare(combStr, reactionStr, minMismatch);
        if(nMismatch < minMismatch)
        {
            minMismatch = nMismatch;
                                    /*clear old result */
            clearResult(AlleleArray1, AlleleArray2);
        }
                                    /*store new result */
        writeResult (A1, A2, AlleleArray1, AlleleArray2);
        }
    }
    /*
    ** post process result:
    ** count number of changed digits, make group call, sort candidate
    assignments, etc.
    */
    PostProcessAlleleResult(AlleleArray1, AlleleArray2);
}
/* Genetic CrossMatching */
main( )
{
    /*
    ** Generate reaction pattern by digitizing experimental interaction pattern
    ** comprising selected marker alleles
    */
    ReactionPattern = GenerateRecipientGenotype(ExpIntPattern, Thresholds);
    /*
    ** Assign Haplotypes by computing all biallelic combinations of known or
    ** possible alleles; reaction patterns of such alleles with the probes in the
    ** selected set are stored ** in a HitTable; return a pointer to a list of all
    ** compatible alleles or haplotypes
    */
    AssignAlleles(AlleleArray1, AlleleAray2, ReactionStr, HitTable);
    /*
    ** Apply string matching (optionally with weighted distance function) to
    select ** all compatible donors
    */
    SelectCompatibleDonors(DonorRegistry, RecipientHaplotypes);
}
```

TABLE 1

HEA-panel composition showing blood groups and associated SNPs

| Blood Group | Phenotype | Polymorphism |
|---|---|---|
| Colton | $Co^a/Co^b$ | 134 C > T |
| Diego | $Di^b/Di^a$ | 2561 C > T |
| Duffy | $Fy^a/Fy^b$ | 125 G > A |
|  | $Fy^x$ [Fy(b+$^w$)] | 265 C > T |
|  | GATA (Fy(a−b−) | −33 T > C |
| Dombrock | $Do^a/Do^b$ | 378 C > T |
|  |  | 624 T > C |
|  |  | 793 A > G |
|  | Hy+/Hy− | 323 G > T |
|  | Jo(a+)/Jo(a−) | 350 C > T |
| Kidd | $Jk^a/Jk^b$ | 838 G > A |
| Kell | K/k | 698 T > C |
| Landsteiner-Wiener | $LW^a/LW^b$ | 308 A > G |
| Lutheran | $Lu^a/Lu^b$ | 230 A > G |
| MNS | GYPA (M/N) | 59 C > T |
|  | GYPB (S/s) | 143 T > C |
| Scianna | Sc1/Sc2 | 169 G > A |
| Rh | S68N (C/c) | 203 A > G |
| Rh | A226P (E/e) | 676 G > C |
| Hemoglobin S | HbS | 173 A > T |

TABLE 2

Rh-panel composition showing AA change and associated SNPs

| Exon | Amino acid change | Polymorphism |
|---|---|---|
| 1 | W16C | 48 G > C |
| 2 | L60I | 178 C > A |
| 2 | S68N | 203 A > G |
| 2 | P103S | 307 C > T |
| 3 | N152T | 455 A > C |
| 4 |  | 37 bp dup.-ins.* |
| 5 | F223V | 667 T > G |
| 5 | A226P | 676 G > C |
| 5 | E233Q | 697 G > C |
| 5 | L245V | 733 G > C |
| 7 | G336C | 1006 G > T |

*known as "pseudoD"

In the sequence listings attached, for the various exons 1, 2, 3, 5 or 7, the primer sequence of the forward and/or reverse primer (as indicated) is indicated with a "check" mark on the sequence listing, and the sequence of the other primer in the set (forward or reverse, as applicable) is shown in Table 3, as follows:

TABLE 3

| | |
|---|---|
| Exon 1: reverse primer: Rh CE 5' GCT ATT TGC TCC TTT GAC CAC 3' | (SEQ ID NO.:1) |
| Exon 2: forward primer RhD: TCT CCC CAC AGA GCA GTT | (SEQ ID NO.:2) |
| Exon 3: reverse primer Rh CE: CCT CAA GTG ATC TGC CTT CCT CAG | (SEQ ID NO.:3) |
| Exon 5: reverse primer Rh CE: TGC TCA CCA TTC TGA TCT TCC T | (SEQ ID NO.:4) |
| Exon 7: reverse primer Rh CE: CAT CTC CGT CAG GCA CTC CAT | (SEQ ID NO.:5) |

A number of other markers and alleles may also be assayed using the methods described herein, including HpA.

Dombrock: Two New Alleles—By probing five common mutations at positions Do-793, Do-624, Do-378, Do-350 and Do-323, using, for example, RFLP analysis, four alleles have been identified to date (Table 4):

TABLE 4

| | DO-793 | DO-624 | DO-378 | DO-350 | DO-323 |
|---|---|---|---|---|---|
| DoA | A | A | A | A | A |
| DoB | B | B | B | A | A |
| Hy | B | B | A | A | B |
| Jo | A | A | B | B | A |

BeadChip eMAP Design—In accordance with the format of elongation-mediated multiplexed analysis of polymorphisms (eMAP), pairs of encoded elongation probes were designed to interrogate the target at the five designated positions, selecting, in each pair, one probe matching the expected normal ("wild type") and a second probe differing from the first at or near the 3' terminus and matching the anticipated variant. Primers are used to generate amplicons serving as target sequences for subsequent elongation analysis, where the amplicons either include subsequences corresponding or complementary to the subsequences at, and proximal to the designated polymorphic sites, or which correspond or are complementary in whole to such subsequences. In the alternative, it is possible to generate sufficient concentration of the genomic DNA in the sample without amplification to allow their targeting, hybridization and elongation, using complementary probes and appropriate elongation conditions. An eMAP design incorporating in a single BeadChip probe pairs for all five mutations of interest, was used to analyze a subset of 63 samples, selected from a cohort of ~430 controls and clinical samples. The results are shown below in Table 5

TABLE 5

| DO-793 | DO-624 | DO-378 | DO-350 | DO-323 | | Cases | Freq |
|---|---|---|---|---|---|---|---|
| −1 | −1 | −1 | 1 | 1 | DoB/DoB | 14 | 0.22 |
| −1 | −1 | 0 | 1 | 0 | DoB/Hy | 17 | 0.27 |
| −1 | −1 | 0 | 1 | 1 | DoB/Sh | 3 | 0.05 |
| −1 | −1 | 1 | 1 | −1 | Hy/Hy | 1 | 0.02 |
| −1 | −1 | 1 | 1 | 0 | Hy/Sh | 1 | 0.02 |
| −1 | −1 | 1 | 1 | 1 | Sh/Sh | 0 | 0 |
| 0 | 0 | −1 | 0 | 1 | DoB/Jo | 2 | 0.03 |
| 0 | 0 | −1 | 1 | 1 | DoB/Ha | 5 | 0.08 |
| 0 | 0 | 0 | 1 | 1 | DoA/DoB | 11 | 0.17 |
| 0 | 0 | 0 | 1 | 1 | Hy/Ha | | |
| 0 | 0 | 0 | 1 | 1 | Ha/Sh | | |
| 0 | 0 | 0 | 1 | 1 | Jo/Sh | 0 | 0 |

TABLE 5-continued

| DO-793 | DO-624 | DO-378 | DO-350 | DO-323 | | Cases | Freq |
|---|---|---|---|---|---|---|---|
| 0 | 0 | 0 | 0 | 0 | Hy/Jo | 0 | 0 |
| 0 | 0 | 1 | 1 | 0 | DoA/Hy | 1 | 0.02 |
| 0 | 0 | 1 | 1 | 1 | DoA/Sh | 0 | 0 |
| 1 | 1 | −1 | −1 | 1 | Jo/Jo | 0 | 0 |
| 1 | 1 | −1 | 0 | 1 | Jo/Ha | 0 | 0 |
| 1 | 1 | −1 | 1 | 1 | Ha/Ha | 0 | 0 |
| 1 | 1 | 0 | 0 | 1 | DoA/Jo | 5 | 0.08 |
| 1 | 1 | 0 | 1 | 1 | DoA/Ha | 2 | 0.03 |
| 1 | 1 | 1 | 1 | 1 | DoA/DoA | 1 | 0.02 |
| | | | | | | 63 | |

Four new allele combinations, highlighted in bold face font in Table 5 (DoB/Sh; Hy/Dh; DoB/Ha; DoA/Ha) are evident—wherein 1, 0 and −1 respectively denote allele combinations AA, AB or BA and BB.

TABLE 6

| | DO-793 | DO-624 | DO-378 | DO-350 | DO-323 |
|---|---|---|---|---|---|
| Ha | A | A | B | A | A |
| Sh | B | B | A | A | A |

These four combinations, which have been confirmed by sequencing of the corresponding amplicons, are readily shown to represent the combination of known alleles with two new alleles, namely (Table 6): That is, Ha differs from DoA, and Sh differs from DoB, by the replacement of, respectively, A by B and B by A in position Do-378. As a result, the combination of Ha and Sh generates the same string ("word"), namely 00011, as does the combination DoA/DoB; similarly, Hy/Ha also generates the same string. This degeneracy may account for the relatively high frequency of occurrence of that string, suggesting that observation of 000 in a first pass of analysis may be misattributed to the occurrence of DoA/DoB. However, the two 5-letter strings remain degenerate, and resolution of this ambiguity must invoke analysis of additional markers.

The six Dombrock alleles including the two new alleles identified herein generate the following 21 combinations.

TABLE 7

| | DoB | | | | | Hy | | | | | Sh | | | | | Jo | | | | | Ha | | | | | DoA | | | | |
|---|---|---|---|---|---|---|---|---|---|---|---|---|---|---|---|---|---|---|---|---|---|---|---|---|---|---|---|---|---|---|
| DoB | -1 | -1 | -1 | 1 | 1 | -1 | -1 | 0 | 1 | 0 | -1 | -1 | 0 | 1 | 1 | 0 | 0 | -1 | 0 | 1 | 0 | 0 | -1 | 1 | 1 | 0 | 0 | 0 | 1 | 1 |
| Hy | | | | | | -1 | -1 | 1 | 1 | 1 | -1 | -1 | -1 | 1 | 1 | 0 | 0 | 0 | 0 | 0 | 0 | 0 | 0 | 1 | 1 | 0 | 0 | 1 | 1 | 0 |
| Sh | | | | | | | | | | | -1 | -1 | 1 | 1 | 1 | 0 | 0 | 0 | 0 | 1 | 0 | 0 | 0 | 1 | 1 | 0 | 0 | 1 | 1 | 1 |
| Jo | | | | | | | | | | | | | | | | 1 | 1 | -1 | -1 | 1 | 1 | 1 | -1 | 0 | 1 | 1 | 1 | 0 | 0 | 1 |
| Ha | | | | | | | | | | | | | | | | | | | | | 1 | 1 | -1 | 1 | 1 | 1 | 1 | 0 | 1 | 1 |
| DoA | | | | | | | | | | | | | | | | | | | | | | | | | | 1 | 1 | 1 | 1 | 1 |

As indicated in the Table 7, at the resolution provided by the first three Dombrock polymorphisms, namely DO-793, -624 and -378, several of the 3-letter allele combinations are degenerate. Complete resolution of the degeneracy of the allele combinations will require determination of polymorphisms beyond the current five.

Silencing Mutations: Duffy and GATA—The expression of an antigen can be affected by silencing mutations, for example in the GATA box of the gene encoding Duffy (Fy). Thus to establish allele combinations of the markers Fy 125 T>C and GA-33 T>C, especially in the case of a heterozygous GA marker, may call for phasing, as described below.

Automated Allele Assignment: Hit Table—The process of selecting allele combinations which match or partially match a particular experimental pattern produced by eMAP preferably employs a hit table (such as Table 8 below) for the five Dombrock polymorphisms described above. Using the hit table in conjunction with a listing of known alleles, an algorithm of pattern matching can be applied to select, in automated fashion, matching or partially matching combinations of alleles which can be reviewed and edited in an integrated software environment such as that provided by the Automated Allele Assignment (AAA) program, described in U.S. application Ser. No. 10/909,638, incorporated by reference. In Table 8, "8" denotes a positive assay signal, indicating, for example, probe elongation, and "1" denotes a negative assay signal, indicating, for example, lack of probe elongation.

TABLE 8

HIT TABLE

| | N | V | N | V | N | V | N | V | N | V |
|---|---|---|---|---|---|---|---|---|---|---|
| DoA | 8 | 1 | 8 | 1 | 8 | 1 | 8 | 1 | 8 | 1 |
| DoB | 1 | 8 | 1 | 8 | 1 | 8 | 8 | 1 | 8 | 1 |
| Hy | 1 | 8 | 1 | 8 | 8 | 1 | 8 | 1 | 1 | 8 |
| Jo | 8 | 1 | 8 | 1 | 1 | 8 | 1 | 8 | 8 | 1 |
| Ha | 8 | 1 | 8 | 1 | 1 | 8 | 8 | 1 | 8 | 1 |
| Sh | 1 | 8 | 1 | 8 | 8 | 1 | 8 | 1 | 8 | 1 |

RULES 8 == matched, 1 == mismatched
8 OR 8 = 8, 1 OR 1 = 1, 8 OR 1 = 1, 1 OR 8 = 8
Example DoB/Sh

| | | | | | | | | | | |
|---|---|---|---|---|---|---|---|---|---|---|
| Reaction Pattern | 1 | 8 | 1 | 8 | 8 | 8 | 8 | 1 | 8 | 1 |
| Allele Combination | | -1 | | -1 | | 0 | | 1 | | 1 |

Haplotype Determination with Phasing—One method of distinguishing haplotypes (combinations of alleles on the same homolog) is to use phasing, as disclosed in U.S. application Ser. No. 10/271,602;International Application No. WO03034029 (incorporated by reference). Phasing involves generating an elongation product from a probe capable of detecting a first polymorphic target site, and then determining if counterparts of other designated polymorphic sites are present within that elongation product. If so, this indicates that the two markers including both the first and the other designated polymorphic sites belong to the same allele.

More particularly, phasing is carried out by using encoded beads displaying elongation probes, which thereby identify both the probes and elongation products, and then annealing to the elongation product labeled oligonucleotide probes to determine whether or not counterpart(s) of additional polymorphic sites are present within the elongation product. By interrogating elongation products generated from probes directed toward a series of successive designated polymorphic sites, the phase of the combination of alleles generating a reaction pattern can be determined.

It should be understood that the terms, expressions and examples hereinabove are exemplary only and not limiting, and that the invention is defined only in the claims which follow, and includes all equivalents of the subject matter of those claims.

What is claimed is:

1. A method of selecting a transfusion donor by determination of compatibility to a recipient by comparing combinations of polymorphic markers in a set of such markers, of candidate donors and a recipient where said determination is performed following subjecting genomic material/DNA from candidate donors and the recipient to amplification to thereby generate amplified products; wherein the amplified products are further subjected to a hybridization assay or to a capture-mediated elongation assay, or both, wherein an assay signal is generated by the individual hybridization or elongation events, as applicable, by pairs of probes wherein pair members are complementary, in whole or in part, to the subsequences of the amplified products which are the same as (and/or which are complementary to) polymorphic markers in the set;

and an assay signal intensity pattern is generated from hybridization or elongation events such that each marker in the set is represented by a pair of particular assay signal intensities, the method comprising: determining the assay signal intensity pattern generated by said hybridization or elongation assay and forming, for each probe pair, a combination of signal intensities associated with the members of the pair;

generating, from said combinations of signal intensities, a series of values, each value in the series selected from one of three possible values, respectively indicating a state of homozygous-normal, heterozygous or homozygous-variant to thereby form a ternary reaction pattern;

determining the polymorphic marker combinations represented by said ternary reaction pattern; and selecting from the candidate donors a donor having said polymorphic marker combination identical to that of the recipient.

2. The method of claim 1 wherein polymorphic sites within the markers are known to affect the transcription or expression of clinically relevant antigens.

3. The method of claim 1 wherein combination of signal intensities of members are represented such that one such intensity, $i_N$, correlates with the amount of normal marker in the sample, and the other such intensity, $i_V$, correlates with the amount of variant marker in the sample, and said intensities are combined to form a discrimination parameter $\Delta = (i_N - i_V)/(i_N + i_V)$, which varies between −1 and 1.

4. The method of claim 3 wherein the ternary reaction pattern is generated by designating values of the discrimination parameter below a first threshold as a lower value, designating values of the discrimination parameter above a second threshold as an upper value, and designating values of the discrimination parameter below the second threshold but above the first threshold as an intermediate value.

5. The method of claim 4 wherein when the assay is a hybridization assay wherein the signal intensity pattern is converted to the ternary reaction pattern by forming ratios of signal intensities associated with a probe pair and designating the sample as homozygous for a marker for ratios above a first threshold, and designating the sample as homozygous for the marker for a variant allele for ratios below a second threshold, and designating the sample as heterozygous for the marker ratios below the first threshold and above the second threshold.

6. The method of claim 4 wherein the first threshold is a lower threshold and the second threshold is an upper threshold.

7. The method of claim 4 wherein the values of the discrimination parameter below the first threshold are designated by a −1, the values above second threshold are designated by a +1, and the values between the upper and lower thresholds are designated by a 0.

8. The method of claim 1 wherein, an ambiguity arises because more than one polymorphic marker combination is represented by the ternary reaction pattern, an additional assay step is performed on at least one of the amplified products including the subsequences (or the single nucleotide polymorphic sites) of the amplified products which are the same as and/or are complementary to at least one of said markers in said combination, to thereby resolve the ambiguity.

9. The method of claim 8 wherein the additional assay step is hybridization, where annealing of an oligonucleotide to a marker in an amplified product indicates the presence of one of the subsequences in the amplified product.

10. The method of claim 8 wherein the additional assay step is capture-mediated probe elongation, where elongation of an oligonucleotide following annealing to a subsequence in an amplified product indicates the presence of one of the markers in the amplified product.

11. The method of claim 10 wherein elongation products incorporate a labeled ddNTP or a labeled dNTP.

12. The method of claim 11 wherein the dNTPs or ddNTPs are labeled so as to generate optically detectable assay signals when incorporated into elongation products.

13. The method of claims 11 or 12 wherein the label is fluorescence.

14. The method of claim 1 wherein the polymorphic markers are included in the following blood groups, and associated with the corresponding phenotypes as listed:

| Blood Group | Phenotype | Markers |
|---|---|---|
| Colton | $Co^a/Co^b$ | 134 C or T |
| Diego | $Di^b/Di^a$ | 2561 C or T |
| Duffy | $Fy^a/Fy^b$ | 125 G or A |
|  | $Fy^x$ [Fy(b+$^w$)] | 265 C or T |
|  | GATA (Fy(a−b−)) | −33 T or C |

-continued

| Blood Group | Phenotype | Markers |
|---|---|---|
| Dombrock | $Do^a/Do^b$ | 378 C or T |
|  |  | 624 T or C |
|  |  | 793 A or G |
|  | Hy+/Hy− | 323 G or T |
|  | Jo(a+)/Jo(a−) | 350 C or T |
| Kidd | $Jk^a/Jk^b$ | 838 G or A |
| Kell | K/k | 698 T or C |
| Landsteiner-Wiener | $LW^a/LW^b$ | 308 A or G |
| Lutheran | $Lu^a/Lu^b$ | 230 A or G |
| MNS | GYPA (M/N) | 59 C or T |
|  | GYPB (S/s) | 143 T or C |
| Scianna | Sc1/Sc2 | 169 G or A |
| Rh | S68N (C/c) | 203 A or G |
| Rh | A226P (E/e) | 676 G or C |
| Hemoglobin S | HbS | 173 A or T. |

15. The method of claim 1 wherein the polymorphic markers are included in the blood groups RhCE and RhD and the markers are as listed:

| Exon | Markers |
|---|---|
| 1 | 48 G or C |
| 2 | 178 C or A |
|  | 203 A or G |
|  | 307 C or T |
| 3 | 455 A or C |
| 4 | 37 bp dup.-ins. |
| 5 | 667 T or G |
| 5 | 676 G or C |
| 5 | 697 G or C |
| 5 | 733 G or C |
| 7 | 1006 G or T. |

16. The method of claim 1 wherein the amplified products are amplicons or transcripts.

17. The method of claim 1 wherein the amplified products are generated by performing polymerase chain reaction or reverse transcription on samples of genomic DNA or RNA, respectively.

18. The method of claim 17 further including the step of generating single-stranded amplified products.

19. The method of claim 18 wherein the single-stranded amplified products are generated by phosphorylating one of the target strands and then enzymatically digesting it.

20. The method of claim 1 wherein the assay signal intensities used in comparison are normalized intensity ratios.

21. The method of claim 1 wherein the probes are encoded by displaying them on encoded carriers that permit identification of the associated probe.

22. The method of claim 21 wherein the encoded carriers are microparticles.

23. The method of claim 21 wherein the encoding is with color.

24. The method of claim 1 wherein the polymorphic markers are associated with minor blood group types.

25. The method of claim 1 wherein donor constituent allele combinations are collated in a registry that may be queried electronically.

* * * * *